US010588513B2

(12) United States Patent
Dholakia et al.

(10) Patent No.: US 10,588,513 B2
(45) Date of Patent: Mar. 17, 2020

(54) OPTICAL APPARATUS FOR USE WITH A MEDICAL IMAGER

(71) Applicant: University Court of the University of St Andrews, St Andrews (GB)

(72) Inventors: Kishan Dholakia, St Andrews (GB); Praveen Cheriyan Ashok, St Andrews (GB)

(73) Assignee: UNIVERSITY COURT OF THE UNIVERSITY OF ST ANDREWS, St Andrews Fife (GB)

(*) Notice: Subject to any disclaimer, the term of this patent is extended or adjusted under 35 U.S.C. 154(b) by 605 days.

(21) Appl. No.: 14/650,524

(22) PCT Filed: Jan. 20, 2014

(86) PCT No.: PCT/GB2014/050147
§ 371 (c)(1),
(2) Date: Jun. 8, 2015

(87) PCT Pub. No.: WO2014/114921
PCT Pub. Date: Jul. 31, 2014

(65) Prior Publication Data
US 2015/0313471 A1    Nov. 5, 2015

(30) Foreign Application Priority Data

Jan. 24, 2013  (GB) .................................. 1301280.2

(51) Int. Cl.
*A61B 5/00*    (2006.01)
*A61B 1/07*    (2006.01)
(Continued)

(52) U.S. Cl.
CPC .............. *A61B 5/0075* (2013.01); *A61B 1/07* (2013.01); *A61B 5/0035* (2013.01);
(Continued)

(58) Field of Classification Search
CPC .. A61B 5/0075; A61B 5/0084; A61B 10/0233
See application file for complete search history.

(56) References Cited

U.S. PATENT DOCUMENTS 5,963,319 A * 10/1999 Jarvis ........................ G01J 3/44
356/301
6,013,024 A    1/2000 Mitsuda et al.
(Continued)

FOREIGN PATENT DOCUMENTS

DE    102007045988 A1    10/2008
EP        1356773 A1    10/2003
(Continued)

OTHER PUBLICATIONS

"Combined Diffuse Optical Tomography (DOT) and MRI system for Cancer Imaging in Small Animals" by Gulsen et al. Technology in Cancer Research and Treatment. vol. 5, No. 4. 2006.*
(Continued)

*Primary Examiner* — Baisakhi Roy
*Assistant Examiner* — Jason M Ip
(74) *Attorney, Agent, or Firm* — Alston & Bird LLP

(57) ABSTRACT

An optical apparatus comprising a disposable non-magnetic optical fibre probe for coupling light into a sample and receiving light from the sample for performing Raman spectroscopy, and a non-magnetic optical extension releasably connected to the disposable non-magnetic optical probe for transmitting light into the disposable non-magnetic optical probe and receiving light from the disposable non-magnetic optical probe.

19 Claims, 5 Drawing Sheets

(51) Int. Cl.
*A61B 10/04* (2006.01)
*A61B 5/055* (2006.01)
*A61B 10/02* (2006.01)

(52) U.S. Cl.
CPC ............ *A61B 5/0084* (2013.01); *A61B 5/055* (2013.01); *A61B 5/6848* (2013.01); *A61B 5/6852* (2013.01); *A61B 10/0275* (2013.01); *A61B 10/04* (2013.01); *A61B 2010/045* (2013.01); *A61B 2562/0233* (2013.01); *A61B 2562/164* (2013.01); *A61B 2562/227* (2013.01)

(56) References Cited

U.S. PATENT DOCUMENTS

| | | | | |
|---|---|---|---|---|
| 6,115,523 | A * | 9/2000 | Choi | A61B 1/0017 385/116 |
| 2003/0199753 | A1* | 10/2003 | Hibner | A61B 10/0283 600/411 |
| 2005/0113814 | A1* | 5/2005 | Loeb | A61B 18/22 606/15 |
| 2006/0139633 | A1* | 6/2006 | Puppels | A61B 5/0071 356/301 |
| 2006/0161055 | A1* | 7/2006 | Pewzner | A61B 5/0059 600/310 |
| 2009/0033928 | A1* | 2/2009 | Azimi | G01J 3/02 356/301 |
| 2011/0201965 | A1 | 8/2011 | Hibner et al. | |
| 2011/0218445 | A1 | 9/2011 | Braun et al. | |

FOREIGN PATENT DOCUMENTS

| | | |
|---|---|---|
| EP | 1691190 A1 | 8/2006 |
| JP | 2008-500139 A | 1/2008 |
| JP | 2012-509159 A | 4/2012 |
| WO | WO 2003/087793 A1 | 10/2003 |
| WO | WO 2004/078044 A1 | 9/2004 |
| WO | WO 2005/112778 A1 | 12/2005 |
| WO | WO 2008/095075 A1 | 8/2008 |
| WO | WO 2010/058344 A1 | 5/2010 |
| WO | WO 2010/122443 A2 | 10/2010 |
| WO | WO 2011/153521 A2 | 12/2011 |
| WO | WO 2013/001394 A1 | 1/2013 |

OTHER PUBLICATIONS

International Searching Authority, International Search Report and Written Opinion for International Application No. PCT/GB2014/050147, dated Mar. 14, 2014, 15 pages, European Patent Office, The Netherlands.

Intellectual Property Office, Search Report under Section 17(5) for Application No. GB1301280.2, dated May 22, 2013, 5 pages, United Kingdom.

Japan Patent Office, Office Action for Application No. 2015-554243, dated Dec. 5, 2017, 7 pages, Japan.

* cited by examiner

OPTICAL APPARATUS FOR USE WITH A MEDICAL IMAGER

CROSS REFERENCE TO RELATED APPLICATIONS

This application is a National Stage Application, filed under 35 U.S.C. § 371, of International Application No. PCT/GB2014/050147, filed Jan. 20, 2014, which claims priority to Great Britain Application No. 1301280.2, filed Jan. 24, 2013; the contents of both of which as are hereby incorporated by reference in their entirety.

BACKGROUND

Related Field

The present invention relates to an optical apparatus and method for use with a medical imager. In particular, the invention relates to an apparatus for performing Raman spectroscopy in conjunction with a magnetic resonance imaging scanner.

Description of Related Art

Since the advent of optical microscopy numerous technologies have been developed to obtain morphological and chemical information from tissue. This information plays a key role in disease diagnosis. The development of multi-modal imaging and spectroscopic techniques, which combine two or more technologies, can provide complementary information from tissue and therefore enhance diagnosis.

Magnetic Resonance Imaging (MRI) is an established medical imaging modality, which is being widely used for visualizing internal body structures. MRI has a non-ionizing field that makes it ideal for interventional radiology. However, it remains difficult to implement various procedures with interventional MRI (iMRI), as specialized non-ferromagnetic equipment has to be designed to work in the strong static and dynamic magnetic field of the MRI scanner.

Raman spectroscopy is another powerful tool, which can be used for obtaining bio-chemical information of tissue. The technique is sensitive enough to detect minor changes in the tissue composition for distinguishing between normal and diseased tissue. There has been significant development in the field of fibre Raman probes, which now enables in vivo tissue analysis using endoscopic Raman probes.

Conventional fibre-Raman-probes have an excitation fibre channel and a Raman signal collection fibre channel. These channels are co-aligned at the tip of a probe head. Filters are included at the probe head to reduce fluorescence from the fibre. Such filters may include a line filter to filter out fluorescence background from the excitation fibre and an edge filter that filters out Rayleigh scattered light that would enter the collection channel. The filter assembly at the fibre probe head results in a relatively large probe head. In addition, all commercially available fibre probes comprise metallic ferrules to position micro-optic elements at the probe head.

BRIEF SUMMARY

According to one aspect of the present invention, there is provided an optical apparatus comprising a disposable non-magnetic optical fibre probe for coupling light into a sample and receiving light from the sample, and a non-magnetic optical extension releasably connected to the disposable non-magnetic optical probe for transmitting light into the disposable non-magnetic optical probe and receiving light from the disposable non-magnetic optical probe. The disposable non-magnetic optical probe may be filterless.

By disposable it is meant, the probe is adapted for single use applications. After a single use, the probe is intended to be discarded. The disposable probe may be supplied in a sealed, sterile package.

The disposable non-magnetic optical probe may be adapted to be fitted in a non-magnetic biopsy needle. The non-magnetic biopsy needle may be provided as part of the optical apparatus.

The disposable non-magnetic optical probe may comprise a first optical fibre for coupling light into the sample and at least one second optical fibre for receiving light from the sample. The first and second fibres may be connected at one end to form a probe head. A first optical connector may be provided at another end of the first optical fibre. A second optical connector may be provided at another end of the second optical fibre, wherein the first and second connectors are connectable to the non-magnetic optical extension.

The first optical fibre may have a length less than a critical length to limit fluorescence generation upon optical excitation.

The tips of the first fibre and second fibre may be substantially aligned. Alternatively, the tips of the first and second fibres may be offset, for example the tip of the first fibre may protrude beyond the tip(s) of the second fibre(s) or the tip(s) of the second fibre(s) may protrude beyond the tip of the first fibre. The tips may be offset by less than 10 mm. The offset may be arranged so that in use one of the first and second fibres is in contact with the sample and the other is not.

The first fibre and the second fibre may be substantially parallel in the probe head.

The first fibre and the second fibre may be separated, for example by a gap, in the probe head. The separation of the fibres or gap may be less than 1 mm.

Ideally, the probe head has a diameter less than or equal to 2 mm. The probe head may have at least one optical component, for example one or more lenses.

The non-magnetic optical extension may comprise a first optical extension fibre for transmitting light into the disposable non-magnetic optical probe, and a second optical extension fibre for receiving light from the disposable non-magnetic optical probe.

The non-magnetic optical extension may comprise a first filter for filtering light from the first optical extension fibre and a second filter for filtering light before passing into the second optical extension fibre.

The non-magnetic optical extension may comprise a first optical coupler for coupling light into the disposable non-magnetic optical fibre probe and a second optical coupler for coupling light from the disposable non-magnetic optical fibre probe into the second optical extension fibre.

The non-magnetic optical extension may comprise at least one connector for releasably connecting the extension and the disposable non-magnetic optical probe.

The non-magnetic optical extension may comprise a housing and the first filter and the second filter may be arranged in the housing. The first optical coupler and the second optical coupler may be in the housing. Within the housing, the first filter and/or the first optical coupler may be optically isolated from the second filter and/or the second optical coupler.

The optical apparatus may have a total length greater than a critical length, for example greater than 5 m.

According to another aspect of the invention, there is provided a disposable non-magnetic fibre based optical probe for use in a medical device. The disposable non-magnetic optical probe may be sterile and/or provided in a sterile package. The disposable non-magnetic optical probe may be filterless. The disposable non-magnetic optical probe may comprise a first optical fibre for coupling light into a sample and at least one second optical fibre for receiving light from the sample. A first optical connector may be provided at an end of the first optical fibre. A second optical connector may be provided at an end of the second optical fibre. The first optical fibre may have a length less than a critical length to limit fluorescence generation upon optical excitation. The probe may have a probe head. Preferably, the probe head has a a diameter less than or equal to 2 mm. The probe head may have at least one optical component, for example one or more lenses.

According to yet another aspect of the invention, there is provided a medical system comprising a medical device having a patient area, for example an imaging medical device, and an optical apparatus connected to a light source and a detector, wherein the medical device and the optical apparatus are located in a first room or area and the light source and detector are located in a second room or area electromagnetically shielded from the first. The electromagnetic shielding may include a Faraday cage. The medical device may be an MRI scanner. The light source may be a laser. The detector may include a spectrometer, for example a Raman spectrometer.

According to still another aspect of the present invention, there is provided a method for performing optical spectroscopy measurements on a patient using a probe, a light source and a detector, whilst another medical device is being used, for example an imaging medical device, the method involving monitoring an area of the patient using the medical device and simultaneously moving the probe into the vicinity of the examination area, for example into contact with the examination area, illuminating the examination area using the probe and the light source, collecting light from the excitation area via the probe, and detecting collected light using the detector, wherein the medical device and the probe are located in a first room or area and the light source and detector are located in a second room or area electromagnetically shielded from the first. The medical device may be a MRI scanner. The optical spectroscopy may be Raman spectroscopy.

Bringing a probe head in contact with the examination area may involve inserting a catheter/needle into the area and introducing the probe head inside the catheter/needle.

According to still a further aspect of the invention, there is provided a non-magnetic biopsy needle comprising an elongate tubular portion open at a first end and terminated at a second end by a cutting portion, a window on a wall of the tubular portion, a light reflector inside the tubular portion and optically aligned with the window. The tubular portion may be adapted to receive a disposable non-magnetic optical probe. A transparent sleeve may be located around the window. The window may be located in a region adjacent the cutting portion.

BRIEF DESCRIPTION OF THE FIGURES

Various aspects of the invention will now be described by way of example only and with reference to the accompanying drawings, of which:

FIG. 2 (b) is a cross section of a probe head comprising five collection fibres;

FIG. 2 (c) is an end view of the probe head of FIG. 2 (b);

FIG. 3 (b) is a cross section of a probe head comprising five collection fibres wherein the excitation fiber is the contact fiber;

FIG. 3 (c) is an end view of the probe head of FIG. 3 (b);

FIG. 4 (b) is a cross section of a probe head comprising five collection contact fibres;

FIG. 4 (c) is an end view of the probe head of FIG. 4 (b);

DETAILED DESCRIPTION OF VARIOUS EMBODIMENTS

Figure 1:
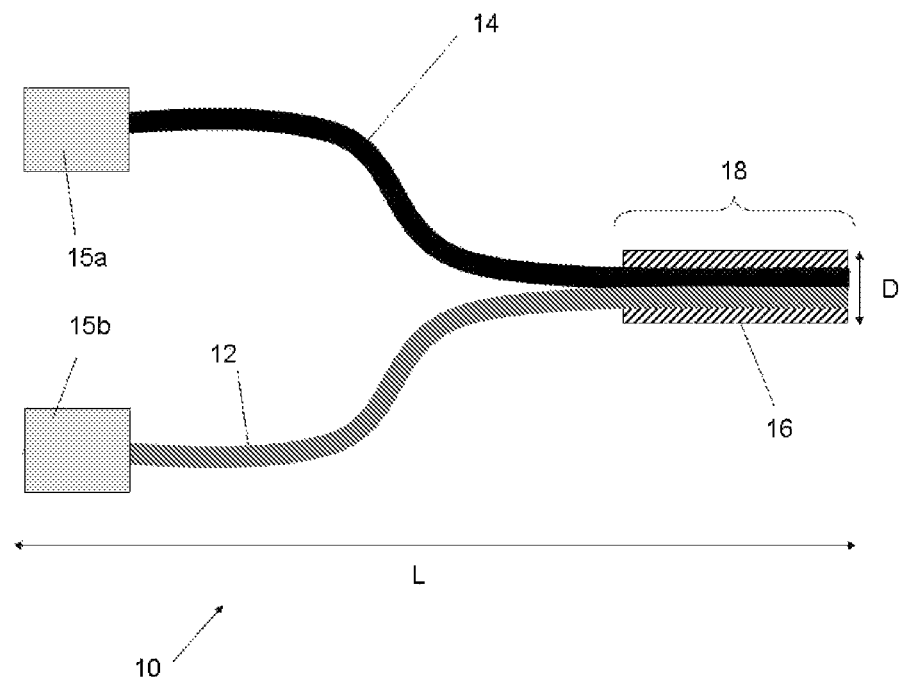
FIG. 1 is a cross section of a disposable non-magnetic optical probe.

FIG. 1 shows a disposable non-magnetic optical probe 10 that has an excitation fibre 12 and a collection fibre 14. At one end, the excitation fibre 12 and the collection fibre 14 are held together by a sleeve 16, such as a heat shrinkable sleeve to form a probe head 18 with a diameter D. Inside the probe head 18, the excitation fibre 12 and the collection fibre 14 are held parallel with their respective ends aligned so as to maximize collection efficiency. At the other end, both the excitation fibre 12 and the collection fibre 14 are terminated with a connector 15a and 15b, such as a SMA or FC-PC connector. All of the components of the probe 10 are non-magnetic. The disposable probe may be sterile and may be supplied in a sealed, sterile package (not shown).

The maximum length L of each fibre in the optical probe 10 is limited by a level of background fluorescence generated inside the excitation fibre 12 compared with a level of signal collected by the collection fibre 14. The fluorescence background is proportional to the level of attenuation of a given optical fibre, which itself varies with an absorption coefficient of the material of the fibre. In the case of a Raman signal emitted from a sample, the level of signal will depend on both the nature of the sample (different samples have different Raman cross sections) and the intensity of radiation used to illuminate the sample. For example, for a Raman measurement of adipose tissue acquired at 785 nm with 200 mW excitation power and an acquisition time of 1 s, the Raman signal was 100 counts for the Raman bands corresponding to methylene scissor deformations and the fluorescence background measured in the excitation optical fibre was 950 counts. In this case, to achieve a signal to background ratio of 0.1, a critical length of 1.5 m is needed. Typically, the fibres of the optical probe 10 have a length L ranging from 0.5 to 1.5 m.

Figure 2:
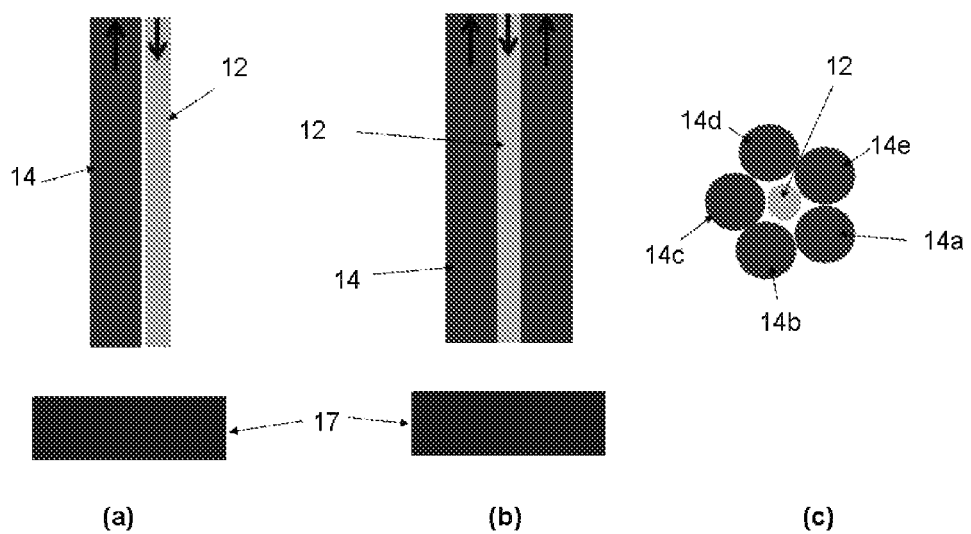
FIG. 2 (a) is a cross section of a probe head comprising a single collection fibre.

FIG. 2 shows two probe heads, one having a single collection fibre (a) and a second (b) having multiple collection fibres aligned around the excitation fibre, as shown in FIG. 2 (c), and bundled together at the distal end opposite the probe head into an optical connector. The tip of the probe head could be polished or cleaved at an angle so that the excitation and collection cones are side looking. Such geometry could be useful when it is necessary to scan tissue surfaces when the probe is inserted into a tube like structure such as an artery.

Figure 3:
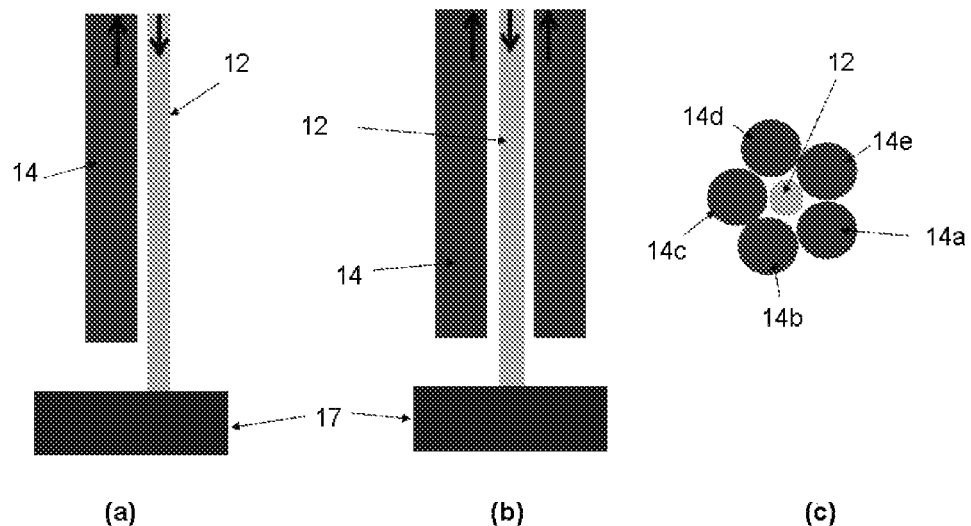
FIG. 3 (a) is a cross section of a probe head comprising a single collection fibre wherein the excitation fiber is the contact fiber.

FIG. 3 (a) shows a probe head that has an excitation fibre 12 that is longer than the collection fibre 14, resulting in an excitation fibre 12 that protrudes beyond the tip of the collection fibre 14 at the end of the probe head. The distance between the tip of the excitation fibre and the tip of the collection fibre may be 3 to 10 mm. In this case, the excitation fibre 12 is shown in contact with a sample 17. The collection fibre 14 is not in contact with the sample 17, but instead is spaced apart from the sample 17.

FIG. 3 (b) shows a probe head having an excitation fibre surrounded by five collection fibres. In this example each one of the five collection fibres has a length that is shorter than the length of the central excitation fibre, resulting in an excitation fibre that protrudes at the tip of the probe head. The distance between the tip of the excitation fibre and the tip of the collection fibres may be in the range of 3 to 10 mm. In this case, the excitation fibre 12 is shown in contact with a sample 17. The collection fibres 14 are not in contact with the sample 17, but instead are all spaced apart from the sample 17.

Figure 4:
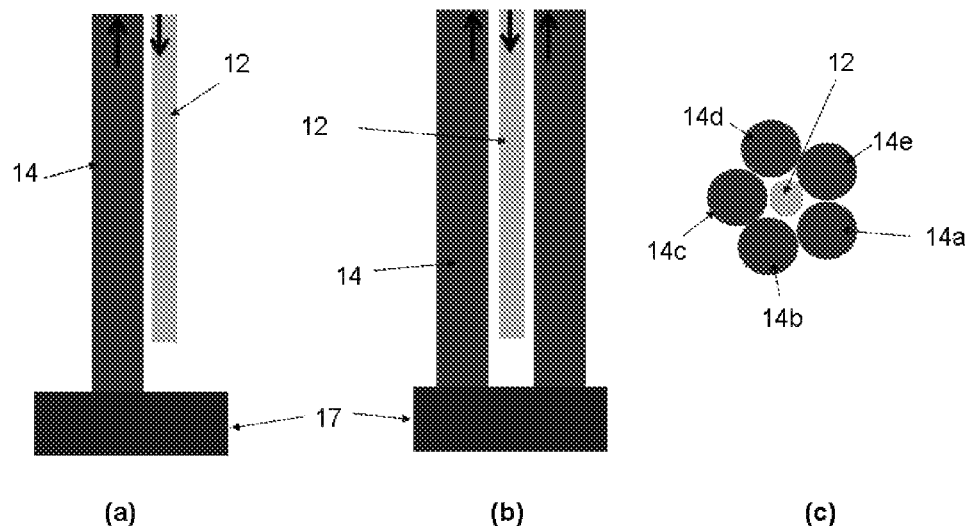
FIG. 4 (a) is a cross section of a probe head comprising a single collection fibre wherein the collection fiber is the contact fiber.

FIG. 4 (a) shows a probe head having an excitation fibre that is shorter than the collection fibre, resulting in a collection fibre that protrudes beyond the end of the excitation fibre at the end of the probe head. The distance between the tip of the excitation fibre and the tip of the collection fibre may be in the range 3 to 10 mm. In this case, the collection fibre 14 is shown in contact with a sample 17. The excitation fibre 12 is not in contact with the sample 17, but instead is spaced apart from the sample 17.

FIG. 4 (b) shows a probe head having a central excitation fibre surrounded by five collection fibres. Each of the five collection fibres has the same length, and each is longer than the central excitation fibre. In this case, the end of the probe has a U-shaped lateral profile. The distance between the tip of the excitation fibre and the tips of the collection fibres may be in the range 3 to 10 mm. In this case, the collection fibres 14 are in contact with a sample 17. The excitation fibre 12 is not in contact with the sample 17, but instead is spaced apart from the sample 17.

The probe head 18 may also contain optical components in order to suit specific applications. For example, the probe head may comprise micro-lenses such as a grin lens assembly, a spherical lens, a ball lens or waveguides, in order to achieve optical focussing or divergence or to enhance the collection efficiency of the probe.

The probe head 18 may be terminated with a glass window to make the probe a contact probe. However, the optical components of the probe head must not contain any metallic substance even if non-ferromagnetic, as this would create artefact in the magnetic resonance images. In addition, to prevent unwanted RF heating, the length of these components should be less than a critical value calculated as a function of the radio frequency (RF) signal produced during MR image acquisition. The critical length for RF heating is calculated as half the wavelength of the RF signal in tissue. In the case of adipose tissue the RF signal has a wavelength of 26 cm, leading to a critical length for the optical components of 13 cm.

Figure 5:
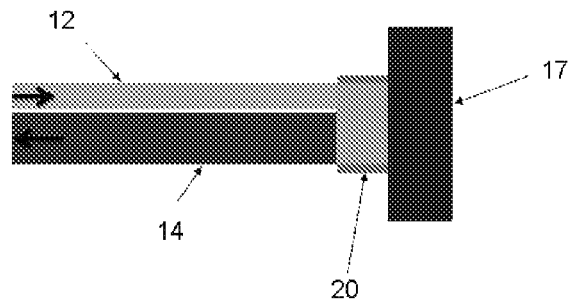
FIG. 5 is a cross section of a probe head comprising an optical window.
Figure 6:
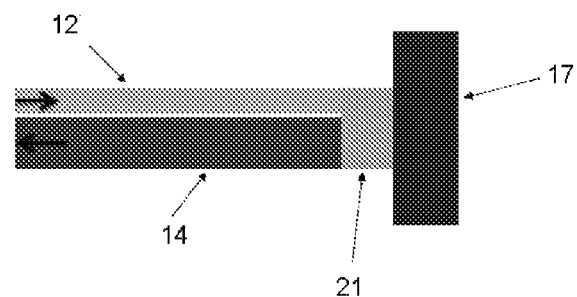
FIG. 6 is a cross section of a probe head comprising a GRIN lens.

FIGS. 5 and 6 show two different probe heads modified to operate as contact probes. In FIG. 5, the probe head is terminated with an optical window 20 that can be put in direct contact with a sample 17. In FIG. 6, the probe head is terminated with a GRIN lens 21. The lens can be put in direct contact with the sample 17 and can also be used to enhance the collection efficiency of the probe.

Figure 7:
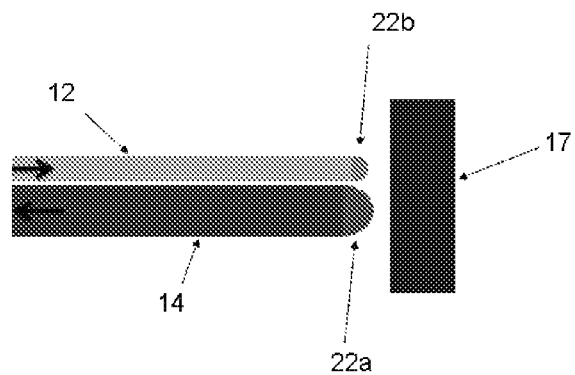
FIG. 7 is a cross section of a probe head comprising two microlenses.
Figure 8:
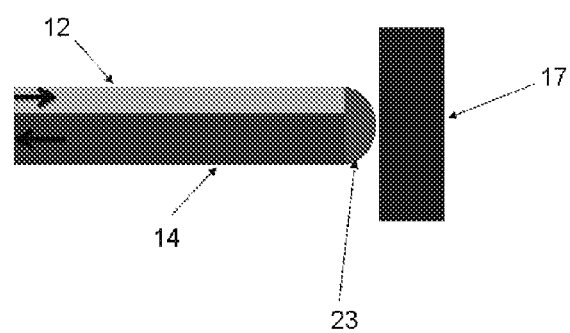
FIG. 8 is a cross section of a probe head comprising one microlens.

FIG. 7 shows a probe head, in which the respective ends of each of the excitation fibre 12 and collection fibre 14 are terminated with a pair of microlenses 22a and 22b. FIG. 8 shows a probe head terminated with a single microlens 23 that covers the tips of the excitation and collection fibres. In both FIGS. 7 and 8, the microlenses may be spherical lenses or ball lenses selected to suit specific applications.

In all cases, the probe head 18 of the disposable optical probe 10 preferably has a diameter less than 2 mm. This allows the probe to be inserted into a surgical device 59 such as biopsy needle or a catheter. The collection and emission fibres may be separated by typically less than 1 mm. For example, the fibres may be separated by a gap of less than 1 mm.

Figure 9:
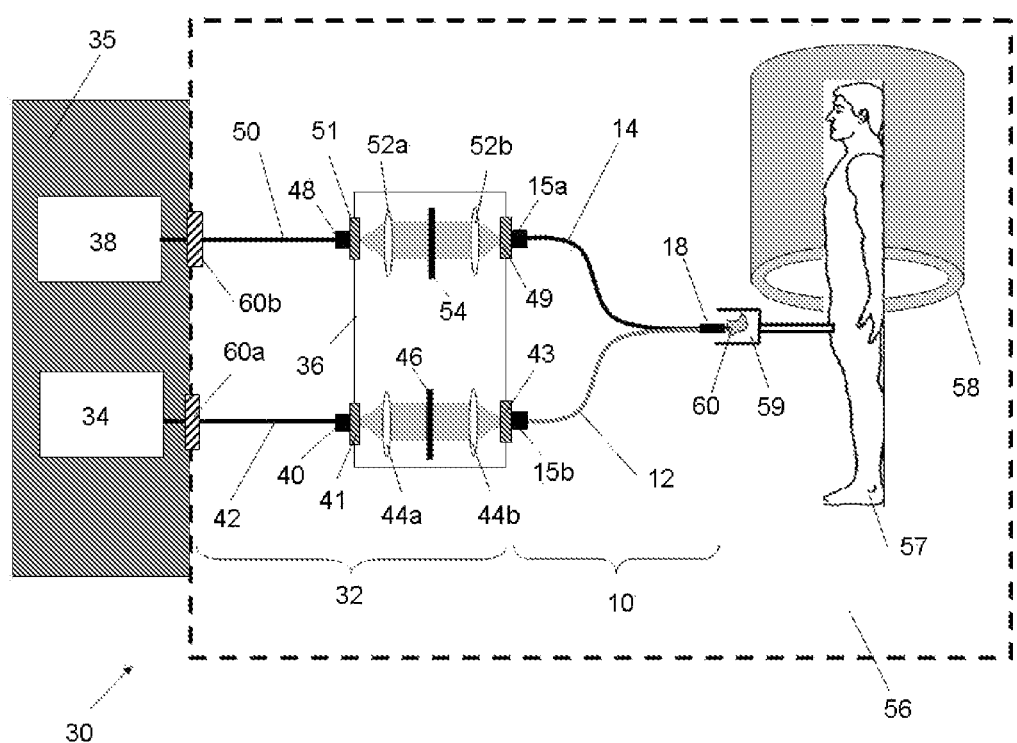
FIG. 9 is a schematic representation of a system for performing optical spectroscopy in an area where a magnetic field is applied.

FIG. 9 shows an optical system 30 implemented in an MRI room 56 where an MRI scanner 58 generates a magnetic field. The optical system 30 comprises a laser 34 and a spectrometer 38 both located inside a control room 35 that is electromagnetically shielded from the MRI room 56, as well as a non-magnetic optical extension 32 and a non-magnetic disposable optical probe 10, both located inside the MRI room 56. Two Faraday cage ports 60a and 60b are provided between the control room 35 and the MRI room 56. The non-magnetic disposable optical 10 probe may be any of the probes described above. The non-magnetic optical extension comprises first and second optical fibre pigtails 42 and 50 and a filtering unit 36.

The filtering unit 36 has an excitation filtering/coupling module arranged between input port 41 and output port 43 and a collection filtering/coupling module arranged between input port 49 and output port 51. Within the housing, the excitation filtering/coupling module and output the collection filtering/coupling module are optically isolated from each other. The excitation filtering/coupling module comprises a pair of lenses 44a and 44b for collimation and refocusing and an excitation filter 46, for example a laser line filter, between the two lenses 44a and 44b. The collection filtering/coupling module has a pair of lenses 52a and 52b for collimation and refocusing and a collection filter 54 for example an edge filter between the two lenses 52a and 52b.

The first fibre pigtail 42 has an optical connector 40 at a first end and a length of exposed fibre at a second end. The first fibre pigtail is connected at the second end to the laser 34 via Faraday cage port 60a and at the first end to the filtering unit 36 via input port 41 by connector 40. The second fibre pigtail 50 has an optical connector 48 at a first end and a length of exposed fibre at a second end. The second fibre pigtail 50 is connected at the second end to the spectrometer 38 via Faraday cage port 60b and at the first end to the filtering unit 36 via output port 51 by connector 48. Alternatively, the first and second fibre pigtails may be directly secured to the filtering unit 36, i.e. without the use of connector/port assembly. In this case, each fibre may be secured permanently to the filtering unit 36.

The excitation fibre 12 of the non-magnetic disposable optical probe 10 is connected to the filtering unit 36 via output port 43 by connector 15b. The collection fibre/bundle 14 of the optical probe 10 is connected to the filtering unit 36 via input port 49 by connector 15a.

The length of the first and second fibre pigtails 42, 50 is chosen to be sufficiently long to bring the optical probe in the proximity of the MRI scanner 58. The first fibre pigtail 42 is less than 5 m long and has a 200 µm diameter. The second fibre pigtail 50 is less than 5 m long and has a 500 µm diameter. All the components of the optical system 30, such as lens mounts, fibre adaptors and cage systems are made of paramagnetic materials, although diamagnetic materials or any non-magnetic materials could equally be used.

The optical system 30 can be used to capture a Raman signal from patient tissue. For example, the system can be used to capture a Raman signal from a biopsy sample 60 extracted during interventional MRI. During such intervention, the patient is subjected to a magnetic field strength in the region of 1.5 to 3 Tesla. A biopsy needle 59 is introduced inside the patient's body 57. The needle 59 is guided toward an area that requires examination by following the magnetic resonance images obtained by the MRI scanner 58. The optical probe 10 is inserted into the biopsy needle 59. Upon activation of the biopsy needle 59 a tissue sample enters the needle's reservoir and comes into contact with the probe head 18.

Once the sample is in contact with the probe head, the laser 34 emits a beam at an excitation wavelength suitable for Raman spectroscopy measurement. The excitation beam propagates through the first pigtail fibre 42 and is directed onto the excitation filtering/coupling module of the filtering unit 36, where the beam is collimated, filtered by the filter 46 to remove background fluorescence and focused onto the excitation fibre 12. The excitation fibre 12 delivers the excitation beam to the apex of the probe head 18 and into the sample 60, causing Raman scattering inside the sample 60. The probe head 18 then collects the back-scattered photons (which include Raman scattered photons) from the sample 60 via the collection fibre 14. The collected light is collimated, filtered by the edge filter 54 to remove out Rayleigh scattered photons and focused onto the second pig tail 50 by the collection filtering/coupling module of the filtering unit 36. The collected light is directed to the Raman spectrometer 38 where a Raman spectrum of the sample is obtained and analysed. The Raman signal can reveal the presence of cancerous tissues.

Alternatively, rather than capturing a Raman signal from a biopsy sample, the probe head could be inserted into a catheter/endoscope and brought into contact with internal tissues. In this case, the tissue is analysed locally by Raman spectroscopy.

When using a fibre based probe for an interventional procedure, it is important to keep the probe head 18 sterile. Disposable probes have to be used, unless it is possible to sterilize the whole probe after each procedure. The use of micro-optic filtering components makes the cost of commercially available fibre Raman probes too expensive to be disposable. However, in the present invention, since there are no filtering elements at the tip of the fibre, it is possible to make the probe 10 disposable.

Figure 10:
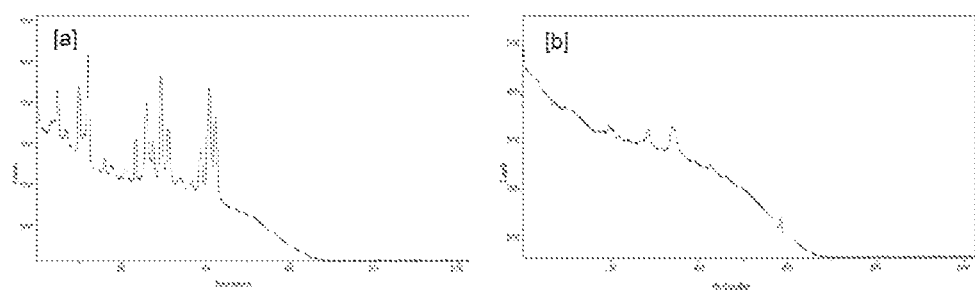
FIG. 10 (a) is a Raman signal of a paracetamol tablet obtained with the optical probe of FIG. 1, and FIG. 10 (b) is a Raman signal of a bovine adipose tissue obtained with the optical probe of FIG. 1.

The collection efficiency of the probe was tested on various samples. FIG. 10a shows a raw Raman spectrum acquired from a paracetamol tablet and FIG. 10b shows a raw Raman spectrum acquired from bovine adipose tissue. The measurements were obtained with 1 s acquisition time and with 200 mW excitation power and an excitation wavelength at 785 nm. It can be observed from both samples that the major Raman peaks are visible in the spectra. The obtained signal was benchmarked with a commercial fibre Raman probe with fibre pigtail length 5 m and the signal to background ratio was found comparable.

The fibre Raman probe described above can be used during MRI guided interventional procedures such as needle biopsy or angioplasty. The probe is adapted to be compatible with MR environment. However, the length of the probe and the disposable probe head makes the design compatible for non-MR surgical environments.

Figure 11:
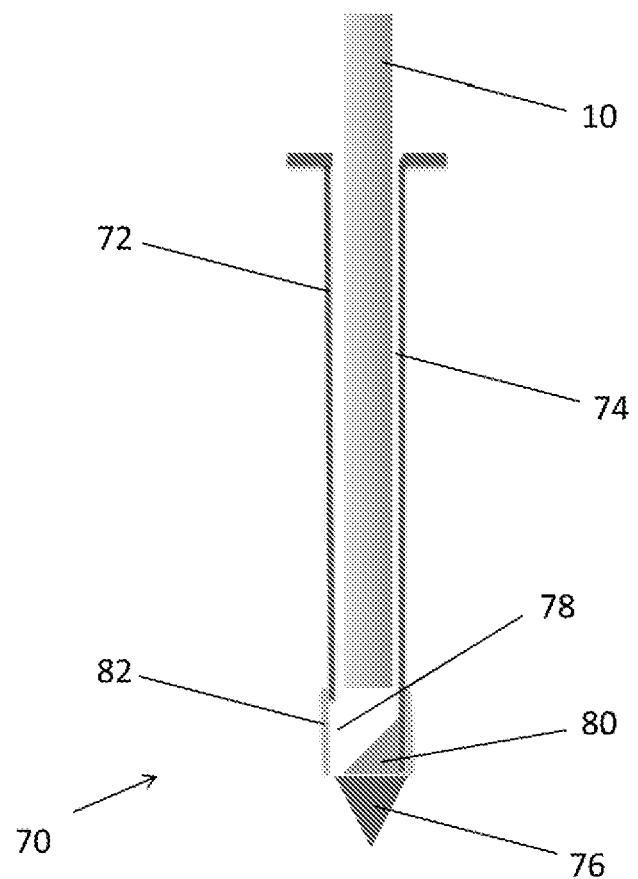
FIG. 11 is a profile sectional view of a non-magnetic optical biopsy needle.
Figure 12:
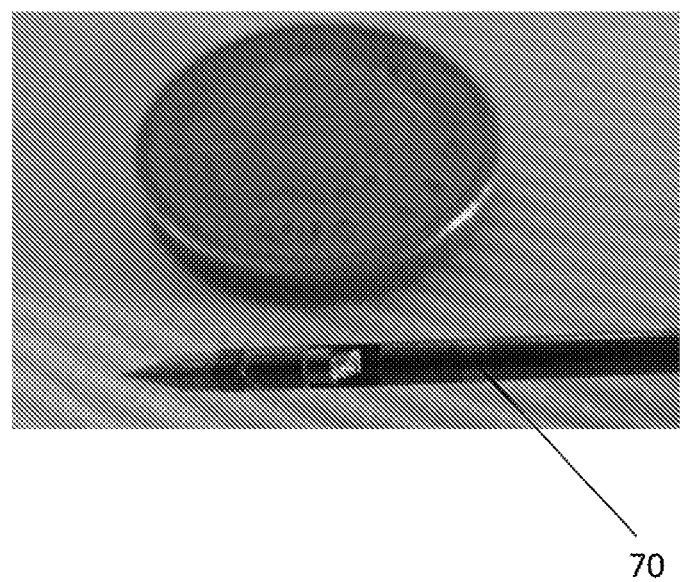
FIG. 12 is a photograph of the optical biopsy needle of FIG. 11.

FIG. 11 shows a magnetic resonance (MR) compatible optical biopsy needle 70. The needle has a tube 72 extending between a first end and a second end and forming a bore 74. Inside the bore 74 is a disposable non-magnetic optical probe 10. The tube 72 is open at the first end and terminated at the second end by a tip 76 for cutting tissue. A window 78 is located on the tube wall at the second end. A micro-prism 80 is fixed inside the bore 74 at a location lying above the tip 76 and positioned such that light emanating from the probe 10 is directed towards the optical window 78 by the prism 80. A transparent heat shrinkable sleeve 82 sits at the second end of the needle 70 around the window 78 and is used to avoid contamination of the optical components during guidance of the needle through tissue. The non-magnetic optical probe 10 is positioned in such a way that the optimal working distance of the probe matches the distance between the tip of the probe 10 and the surface of the protective sheath 82. In this configuration the biopsy needle can operate in contact mode. All of the components of the optical biopsy needle 70 are non-magnetic. FIG. 12 shows a photograph of a biopsy needle 70 next to a one pound coin.

A skilled person will appreciate that variations of the disclosed arrangements are possible without departing from the invention. For example the optical probe and optical system described above are not limited to Raman spectroscopy applications and could be modified to accommodate other type of optical spectroscopy techniques, such as non-linear spectroscopy, fluorescence spectroscopy etc. Also, the disposable non-magnetic optical probe may be non-metallic, as well as non-magnetic. Accordingly, the above description of the specific embodiment is made by way of example only and not for the purposes of limitation. It will be clear to the skilled person that minor modifications may be made without significant changes to the operation described.

The invention claimed is:

1. An optical apparatus comprising:
a disposable non-magnetic optical fibre probe configured for coupling light into a sample and for receiving light from the sample for performing Raman spectroscopy; and
a non-magnetic optical extension releasably connected to the disposable non-magnetic optical fibre probe and configured for transmitting light into the disposable non-magnetic optical fibre probe and for receiving light from the disposable non-magnetic optical fibre probe, wherein:
the disposable non-magnetic optical fibre probe comprises a first optical fibre for coupling light into the sample and a plurality of second optical fibres for receiving light from the sample, the first and second fibres are arranged side-by-side, the first fibre being directly in contact with each second fibre at one end of each of the first and second fibres and connected, at each of said one ends, within a common sleeve to form a probe head, each of the first and second fibres has a corresponding further end opposite said one end, each of the further ends of the first and second fibres being separated from one another, the probe head does not contain any metallic substances, the disposable non-magnetic optical fibre probe is adapted to be fitted in a non-magnetic biopsy needle a tip of each second fibre is aligned in an axial direction with a tip of each of the one or more other second fibres, and the tip of the first fibre protrudes axially beyond the tips of the plurality of second fibres.

2. An optical apparatus as claimed in claim 1, wherein the disposable non-magnetic optical fibre probe is sterile.

3. An optical apparatus as claimed in claim 1, further comprising a non-magnetic biopsy needle.

4. An optical apparatus as claimed in claim 1, wherein the disposable non-magnetic optical fibre probe comprises:
a first optical connector at an end of the first optical fibre that is opposite the probe head, and
a second optical connector at an end of the second optical fibre that is opposite the probe head,
wherein the first and second connectors are connectable to the non-magnetic optical extension.

5. An optical apparatus as claimed in claim 4, wherein the first optical fibre has a length less than a critical length so as to limit fluorescence generation upon optical excitation.

6. An optical apparatus as claimed in claim 5, wherein the critical length is less than 150 cm.

7. An optical apparatus as claimed in claim 1, wherein the probe head has a diameter less than or equal to 2 mm.

8. An optical apparatus as claimed in claim 1, wherein the probe head comprises at least one optical component.

9. An optical apparatus as claimed in claim 1, wherein the non-magnetic optical extension comprises a first optical extension fibre for transmitting light into the disposable non-magnetic optical fibre probe, and a second optical extension fibre for receiving light from the disposable non-magnetic optical fibre probe.

10. An optical apparatus as claimed in claim 9, wherein the non-magnetic optical extension comprises a first filter for filtering light from the first optical extension fibre and a second filter for filtering light into second optical extension fibre.

11. An optical apparatus as claimed in claim 9, wherein the non-magnetic optical extension comprises a first optical coupling lens for coupling light into the disposable non-magnetic optical fibre and a second optical coupling lens for coupling light from the disposable non-magnetic optical fibre into the second optical extension fibre.

12. An optical apparatus as claimed in claim 1, wherein the non-magnetic optical extension comprises at least one connector for releasably connecting the extension and the disposable non-magnetic optical fibre probe.

13. An optical apparatus as claimed in claim 10, wherein the nonmagnetic optical extension comprises a housing and the first filter and the second filter are arranged in the housing.

14. An optical apparatus as claimed in claim 13, wherein the first optical coupling lens and the second optical coupling lens are in the housing.

15. An optical apparatus as claimed in claim 13, wherein at least one of the first filter or the first optical coupling lens are optically isolated from at least one of the second filter or the second optical coupling lens.

16. An optical apparatus as claimed in claim 1, wherein the optical apparatus has a total length greater than a critical length greater than 3 meters.

17. An optical apparatus as claimed in claim 1, wherein the disposable non-magnetic optical fibre probe is filterless.

18. An optical apparatus as claimed in claim 1, wherein the disposable non-magnetic optical fibre probe comprises a sleeve which holds said one end of the first and second fibres together to form the probe head.

19. An optical apparatus as claimed in claim 18, wherein the sleeve comprises a heat shrinkable sleeve.

* * * * *